United States Patent [19]

Portoghese et al.

[11] Patent Number: 5,298,622

[45] Date of Patent: Mar. 29, 1994

[54] SPIROINDANE OPIATE ANALOGS

[75] Inventors: Philip S. Portoghese; Shigenori Ohkawa, both of St. Paul, Minn.; Scott T. Moe, Salt Lake City, Utah

[73] Assignee: Regents of the University of Minnesota, Minneapolis, Minn.

[21] Appl. No.: 60,638

[22] Filed: May 12, 1993

[51] Int. Cl.$^5$ ................ C07D 489/09; A61K 31/485
[52] U.S. Cl. .................................................. 546/15
[58] Field of Search ......................................... 546/15

[56] References Cited

U.S. PATENT DOCUMENTS

| | | | |
|---|---|---|---|
| 4,440,932 | 4/1984 | Kotick et al. | 546/44 |
| 4,761,429 | 8/1988 | Blum et al. | 514/561 |
| 4,816,586 | 3/1989 | Portoghese | 544/340 |
| 4,882,335 | 11/1989 | Sinclair | 514/282 |
| 5,086,058 | 2/1992 | Sinclair et al. | 514/282 |

FOREIGN PATENT DOCUMENTS

WO85/00970  8/1984  PCT Int'l Appl. .

OTHER PUBLICATIONS

Leland, J. Org. Chem. 48(11) 1813 (1983).
Yamamura, Mark S., et al., Characterization of [$^3$H]Nalrindole Binding to Delta Opioid Receptors in Rat Brain. *Life Sciences*, vol. 50, pp. PL-119-124 (1992).
Jiang, Q., et al., Differential Antagonism of Opioid Delta Antinociception by [D-ala$^2$, Leu$^5$, Cys$^6$] Enkephalin and Naltrindole 5'-Isothiocyanate: Evidence for Delta Receptor Subtypes[1]. *The Journal of Pharmacology and Experimental Therapeutics*, vol. 257, No. 3, pp. 1069-1075 (1991).
Froehlich, J. C., et al., Importance of Delta Opioid Receptors in Maintaining High Alcohol Drinking. *Psychopharmacology*, pp. 467-472 (1991).
Sofuoglu, M. et al., Differential Antagonism of Delta Opioid Agonists by Naltrindole and its Benzofuran Analag (NTB) in Mice: Evidence for Delta Opioid Receptor Subtypes. *The Journal of Pharmacology and Experimental Therapeutics*, pp. 676-680 (1991).
Abdelhamid, Essam E., Selective Blockage of Delta Opioid Receptors Prevents the Development of Morphine Tolerance and Dependence in Mice. *The Journal of Pharmacology and Experimental Therapeutics*, pp. 299-303 (1991).
Froehlich, J. C., Delta Opioid Antagonists Produce Prolonged Supression of Ethanol Intake. *Abstract: The Official Journal of The Research Society on Alcoholism*

(List continued on next page.)

Primary Examiner—Mark L. Berch
Attorney, Agent, or Firm—Warren D. Woessner

[57] ABSTRACT

The present invention provides biologically active compounds of the formulas (I) and (II):

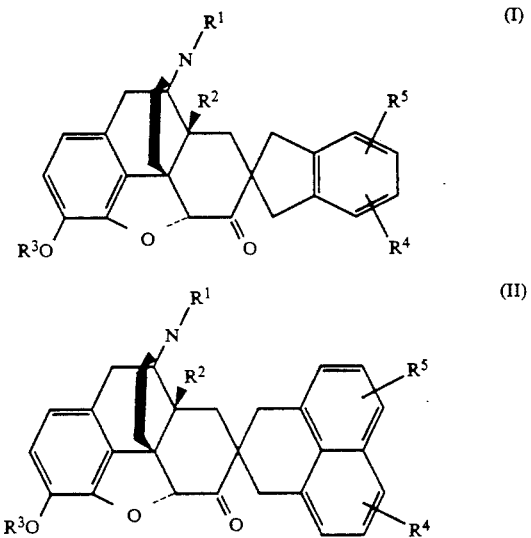

wherein $R^3$ is H or a hydroxyl protecting group, $R^2$ is OH, H or a protected hydroxyl group, $R^1$ is alkyl, cycloalkylalkyl, aryl, aralkyl, cycloalkenylalkyl, alkenyl, allyl or furanylalkyl; and $R^4$ and $R^5$ are individually H, halo, $NO_2$, $NH_2$, ($C_1$-$C_5$)alkyl, ($C_1$-$C_5$)alkoxy, or together are methylene-dioxy or benzo; and the pharmaceutically acceptable salts thereof.

17 Claims, 1 Drawing Sheet

OTHER PUBLICATIONS and International Society for Biomedical Research on Alcoholism vol. 15, No. 2, pp. 315 (1991).

Portoghese, P. S., et al., Role of the Spacer in Conferring Opioid Receptor Selectivity to Bivalent Ligands Related to Norbinaltorphimine. *Journal of Medicinal Chemistry.* pp. 1292–1296 (1991).

Portoghese, P. S., et al., Design of Peptidomimetic Opioid Receptor Antagonists Using the Message-Address Concept. *J. Med. Chem.*, pp. 1714–1720 (1990).

Volpicelli, Joseph R., et al., Naltrexone and the Treatment of Alcohol-Dependence: Initial Observations. *Opioids, Bulimia and Alcohol Abuse and Alcoholism*, pp. 195–214 (1990).

Portoghese, P. S., et al., Naltrindole 5'-Isothiocyanate: A nonequilibrium, Highly Selective Opioid Receptor Antagonists. *J. Med. Chem.*, 33, 1547 (1990).

Froehlic, J. C., Naloxone Attenuates Voluntary Ethanol Intake in Rats Selectively Bred for High Ethanol Preference. *Pharmacology Biochemistry and Behavior*, vol. 35, pp. 385–390 (1990).

Takemori, A. E., et al., Nor-Binaltorphimine, a Highly Selective and Potent Non-Peptide Opioid Receptor Antagonist *European Journal of Pharamacology*, vol. 149, pp. 185–186 (1988).

Portoghese, P.S., et al., Application of the Message-Address Concept in the Design of Highly Potent and Selective Non-Peptide Opioid Receptor Antagonists. *Journal of Med. Chem.*, vol. 31, No. 2, pp. 281–282 (1988).

Portoghese, P. S., et al., Naltrindole, a Highly Selective and Potent Non-Peptide Opioid Receptor Antagonist *European Journal of Pharmacology*, vol. 149, pp. 185–186 (1988).

Takemori, A. E., et al., Evidence for the Interaction of Morphine with Kappan and Delta Opioid Receptors to Induce Analgesia in β-Funaltrexamine-Treated Mice. *The Journal of Pharmacology and Experimental Therapeutics*, vol. 243, No. 1, pp. 91–94 (1987).

Werling, Linda L., et al., Opioid Binding to Rat and Guinea-Pig Neural Membranes in the Presence of Physiological Gations at 37° C. *The Journal of Pharmacology and Experimental Therapeutics*, vol. 233, No. 3, pp. 722–728 (1985).

Martin, William R., Pharmacology of Opioids. *Pharmcological Reviews*, vol. 35, No. 4, pp. 283–323 (1984).

DeLander, Gary E., et al., Role of Spinal Mu Opioid Receptors in the Development of Morphine Tolerance and Dependence. *The Journal of Pharmacology and Experimental Therapeutics*, vol. 231, No. 1, pp. 91–96 (1984).

Cotton, R., et al., ICI 174864: A Highly Selective Antagonist for the Opioid Receptor. *European Journal of Pharmacology*, vol. 97, pp. 331–332 (1984).

Ward, S. L., et al., Pharmacological Characterization in Vivo of the Novel Opiate, β-Funaltrexamine. *The Journal of Pharmacology and Experimental Therapeutics*, vol. 220, No. 3, pp. 494–498 (1982).

Gormley, J. J., et al. In Vivo Evaluation of the Opiate Delta Receptor Antagonists ICI 154, 129. *Life Sciences*, vol. 31., pp. 1263–1266 (1982).

Shaw, J. S., et al., Selective Antagonists at the Opiate Delta-Receptor. *Life Sciences*, vol. 31, pp. 1259–1262 (1982).

Takemori, A. E., et al., The Irreversible Narcotic Antagonistic and Reversible Agonistic Properties of the Fumaramate Methyl Ester Derivative of Naltrexone. *European Journal of Pharmacology*, vol. 70, pp. 445–451 (1981).

Portoghese, Philip S., et al., A Novel Opioid Receptor Site Directed Ankylating Agent with Irreversible Narcotic Antagonistic and Reversible Agonistic Activities. *J. Med. Chem.*, vol.23, pp. 233–234 (1980).

Yano, Ichiro, et al., Inhibition by Naloxone of Tolerance and Dependence in Mice Treated Acutely and Chronically with Morphine. *Research Communications in Chemical Pathology and Pharmacology*, vol. 16, No. 4, pp. 721–734 (1977).

Hayashi, Goro et al., The Type of Analgesic-Receptor Interaction Involved in Certain Analgesic Assays. *European Journal of Pharmacology*, vol. 16, pp. 63–66 (1971).

Leong, Way E., et al., Simultaneous Quantitive Assessment of Morphine Tolerance and Physical Dependence. *The Journal of Pharmacology and Experimental Therapeutics*, vol. 167, No. 1, pp. 1–8 (1969).

Rang, H. P., Stimulant Actions of Volatile Anaesthetics on Smooth Muscle. *Brit. J. Pharmacol.*, vol. 22, pp. 356–365 (1964).

Gates, Marshall, et al., Some Potent Morphine Antagonists Possessing High Analgesic Activity, *J. Med. Chem.*, vol. 7, pp. 127–131 (1964).

Haley, T. J., et al., Pharmacological Effects Produced by Intracerebral Injection of Drugs in the Conscious Mouse. *Brit. J. Pharmacol.*, vol. 12, pp. 12–15 (1957).

SPIROINDANE OPIATE ANALOGS

BACKGROUND OF THE INVENTION

This invention was made with the assistance of the Government under a grant from the National Institutes of Health (Grant No. DA 01533). The U.S. Government has certain rights in the invention.

Endogenous opioid peptides are involved in the mediation or modulation of a variety of mammalian physiological processes, many of which are mimicked by opiates or other non-endogenous opioid ligands. Some of the effects that have been investigated are analgesia, tolerance and dependence, appetite, renal function, gastrointestinal motility, gastric secretion, learning and memory, mental illness, epileptic seizures and other neurological disorders, cardiovascular responses, and respiratory depression.

The fact that the effects of endogenous and exogenous opioids are mediated by at least three different types [mu ($\mu$), delta ($\delta$), kappa ($\kappa$)] of opioid receptors raises the possibility that highly selective exogenous opioid agonist or antagonist ligands might have therapeutic applications. See W. R. Martin, *Pharmacol. Rev.*, 35, 283 (1983). Thus, if a ligand acts at a single opioid receptor type or subtype, the potential side effects mediated through other opioid receptor types can be minimized or eliminated.

The prototypical opioid antagonists, naloxone and naltrexone, are used primarily as pharmacologic research tools and for the reversal of toxic effects of opioids in case of overdose. Since these antagonists act at multiple opioid receptors, their applications in other therapeutic areas or as pharmacologic tools appear to be limited. However, naltrexone recently was reported to reduce the incidence of relapse in recovering alcoholics by J. R. Volpicelli et al., *Opioids, Bulimia and Alcohol Abuse and Alcoholism*, L. D. Reid, ed., Springer-Verlag (1990) at pages 195–214. Naloxone has been reported to suppress ethanol but not water intake in a rat model of alcoholism. J. C. Froehlich et al., Pharm. Biochem. Behav., 35, 385 (1990).

Some progress has been made in the development of highly selective opioid antagonists. For example, Portoghese et al. (U.S. Pat. No. 4,816,586) disclose certain opiate analogs which possess high selectivity and potency at delta receptors. Minimal involvement was observed at mu and kappa opioid receptors. One of the highly selective analogs disclosed in U.S. Pat. No. 4,816,586 has been named "naltrindole" or "NTI," and has the formula (1):

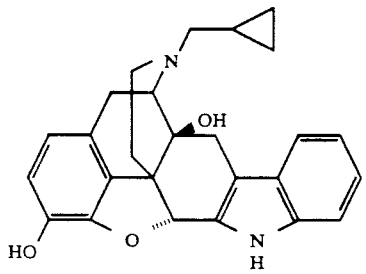

(NTI)

See P. S. Portoghese et al., J. Med. Chem., 31, 281 (1988).

It has recently been reported that suppression of ethanol ingestion may be mediated by the delta opioid receptor type. For example, the $\delta$ antagonist, N,N-diallyl-Tyr-Aib-Aib-Phe-Leu-OH (ICI 174864), strongly inhibits ethanol drinking, but has a very short duration of action, which may limit its clinical utility. See J. C. Froehlich et al., *Psychopharmacol.*, 103, 467 (1991). Using NTI as an antagonist, M. Sofuoglu et al., *J. Pharmacol. Exp. Ther.*, 257, 676 (1991) determined that the antinociceptive activity of two delta receptor agonist enkephalin analogs, DSLET and DPDPE, may be mediated by two discrete delta opioid receptor subtypes. It has also been suggested that development of addiction and/or tolerance to opiates may be inhibited by delta-opioid receptor antagonists, and that opioid-type delta-opioid receptor antagonists may be useful as immunosuppressive agents. Likewise, compounds which are selective at mu receptors may be useful as analgesics which do not exhibit the potentially harmful side effects of less-selective analgesics such as morphine.

Therefore, a continuing need exists for compounds which are opioid receptor-selective, i.e., which can act as agonists or antagonists with specificity at the delta, mu or kappa opioid receptor, or at one of the subtypes of these receptors.

SUMMARY OF THE INVENTION

The present invention is directed to biologically active compounds of the formulas (I) and (II):

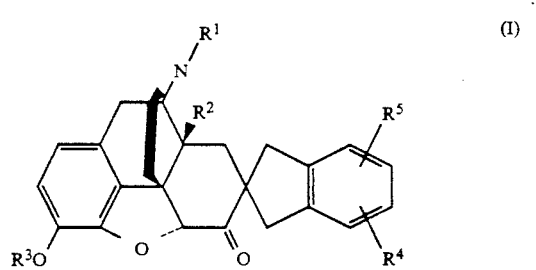

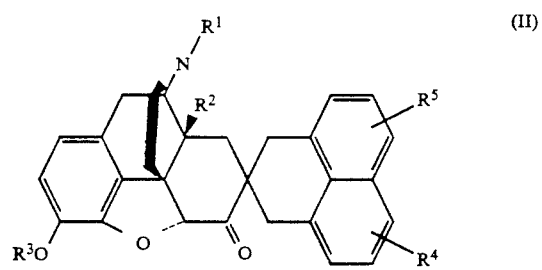

$R^1$ is ($C_1$-$C_5$)alkyl, $C_3$-$C_6$(cycloalkyl)alkyl, $C_5$-$C_7$(cycloalkenyl)alkyl, ($C_6$-$C_{12}$)aryl, ($C_6$-$C_{12}$)aralkyl, trans-($C_4$-$C_5$)alkenyl, allyl or furan-2-ylalkyl, $R^2$ is H, OH or $O_2C(C_1$-$C_5$)alkyl; $R^3$ is H, ($C_6$-$C_{10}$)aralkyl, ($C_1$-$C_5$)alkyl or ($C_1$-$C_5$)alkylCO; and $R^4$ and $R^5$ are individually H, F, Cl, Br, $NO_2$, $NH_2$, ($C_1$-$C_5$)alkyl, ($C_1$-$C_5$)alkoxy or together are dioxymethylene (—$OCH_2O$—) or benzo; and the pharmaceutically acceptable salts thereof.

The present invention also provides a method for blocking opioid receptors, such as mu or delta opioid receptors, in mammalian tissue comprising contacting said receptors in vivo or in vitro with an effective amount of the compound of formula I or II, or mixtures thereof. Using peptide antagonists of known binding selectivity as standards, it was found that the compounds of the invention are antagonists at delta and/or mu receptors. Certain of the compounds are also mixed antagonist/agonists. Thus, the compounds of formula I or II, or mixtures thereof, can be used as pharmacological and biochemical probes of opiate receptor structure and function, e.g., to measure the selectivity of other opioid receptor antagonists or agonists. Such tissue includes tissue of the central nervous system (CNS), the gut, the cardiovascular system, the lung, the kidney, reproductive tract tissue and the like.

The present invention also can provide a method for (a) suppressing ethanol ingestion, (b) or opiate ingestion (self-administration) by a human comprising administering to said human a pharmaceutical unit dosage form comprising an amount of a compound of the formula I or II. It is believed that compounds of formula I or II can decrease opiate or ethanol consumption by mammals without decreasing the intake of food or water for prolonged periods of time. Therefore, it is believed that the compounds of formula I or II will be clinically useful in the treatment of alcoholism or opiate addiction, e.g., that they will be effective to decrease remission rates in recovering alcoholics or addicts. Also, the compounds of formula I or II may be co-administered with morphine, heroin and the like to block the addictive effects without blocking the analgesic effects.

The alkyl moiety present in the $R^1$ group which links the cycloalkyl, cycloalkenyl, aryl, or furan-2-yl moiety to the basic nitrogen atom in the compounds of formula I or II is a lower(alkyl) group, preferably $-(CH_2)_n-$, wherein n is about 1-5, most preferably n is 1, e.g., $R^1$ is $C_3-C_6$(cycloalkyl)methyl, $C_5-C_7$(cycloalkenyl)methyl, arylmethyl or furan-2-yl-methyl. Preferred aryl moieties include $(C_6-C_{10})$aryl, i.e., phenyl, benzyl, tolyl, napthyl, xylyl, anisyl and the like In formula I, or II the position of the $-R^4$ and $-R^5$ groups indicate that they can occupy any available site on the phenyl or naphthyl ring. In structure I or II, a bond designated by a wedged or darkened line indicates one extending above the plane of the $R^3O$-substituted phenyl ring. A bond designated by a broken line indicates one extending below the plane of the phenyl ring.

Preferred compounds of the formula I or II are those wherein $R^1$ is $(C_1-C_5)$alkyl, $C_3-C_6$(cycloalkyl)alkyl or $C_5-C_7$(cycloalkenyl)alkyl, preferably wherein $R^1$ is $C_3-C_6$(cycloalkyl)methyl, and most preferably wherein $R^1$ is cyclopropylmethyl. $R^2$ is preferably OH or OAc ($O_2CCH_3$), and $R^3$ preferably is H. Preferably, at least one, and most preferably, both of $R^4$ and $R^5$ are H, or $R^4$ is H and $R^5$ is benzo, $(C_1-C_4)$alkoxy or nitro. The methylene-dioxy group is preferably a 4,5 or 5,6-methylene-dioxy group.

Since the compounds of the invention are formally morphinan derivatives, it is believed that their ability to cross the "blood-brain barrier" and to affect the central nervous system (CNS) should be far superior to peptide delta opioid antagonists. For example, as disclosed in U.S. patent application Ser. No. 07/750,109, filed Aug. 26, 1991, both NTI and its benzofuran analog, NTB were found to produce unexpectedly prolonged suppression of ethanol drinking without altering water intake in rats that were selectively bred for high voluntary ethanol drinking.

Therefore, the present invention is directed to a method to decrease opiate or ethanol intake by a mammal, such as a human afflicted with alcoholism or alcohol addiction, by administering an amount of a compound or formula I, II or a mixture thereof, that is effective to block delta-opioid receptors, preferably $\delta_1$ opioid receptors, in mammalian tissue.

The present compounds can also be used as immunosuppressive agents in mammals, to facilitate organ transplantation or to suppress autoimmune diseases. The processes of preparing the compounds of formula I or II is also an aspect of the invention, as described hereinbelow.

DETAILED DESCRIPTION OF THE INVENTION

The compounds of formula I or II can be readily synthesized by the double alkylation of a compound of formula III, wherein $R^3$ is a suitable protecting group such as benzyl (Bz), $R^1$ is defined above, and $R^2$ is H, OH or OAlk; with bisbromomethylbenzene or bisbromomethylnaptphalene, or a mono- or di-substituted derivative thereof, in the presence of base, followed by removal of the $R^3$ group to liberate the OH group.

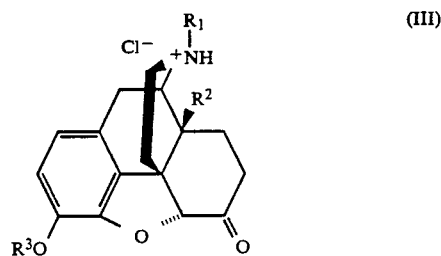

BRIEF DESCRIPTION OF DRAWING

This reaction is illustrated in FIG. 1 by the reaction of 3-benzylnaltrexone (4) with a bisbromomethylbenzene, wherein $R^4$ and $R^5$ are as described above, followed by removal of the benzyl group by hydrogenolysis of intermediate 6 to yield compound 3, wherein $R^4$ and $R^5$ are as described above. Generally, the combination of lithium hexamethydisilazane (LHMDS) and 12-crown-4 in THF gave the best yield of 6. Other crown ethers such as 15-crown-5 and 16-crown-6 are also effective, however, the yield was somewhat lower than when 12-crown-4 is used. Without crown ether, no product was obtained and the starting ketone was recovered. LHMDS in DMSO also afforded 3a low yield.

Bisbromomethylbenzene derivatives (5) are prepared by two methods. The first is by the bromination of xylene derivatives of formula 7 by N-bromusuccinimide (NBS) (Method A) and the other is via the reduction of a bisester (10) or an anhydride (9) with lithium aluminum hydride (LAH), followed by conversion of the bishydroxymethyl groups of 11 to bisbromomethyl groups by $PBr_3$ (Method B).

Method A

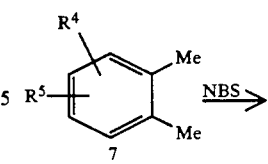

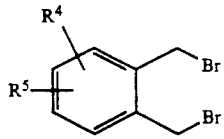

Method B

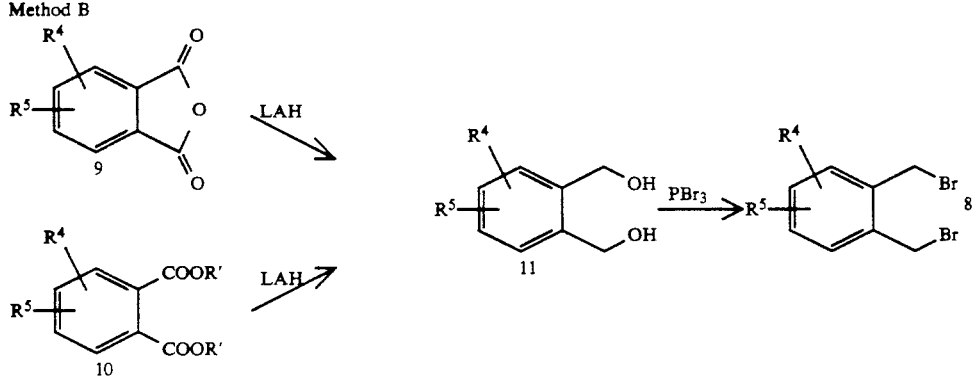

Figure 1:
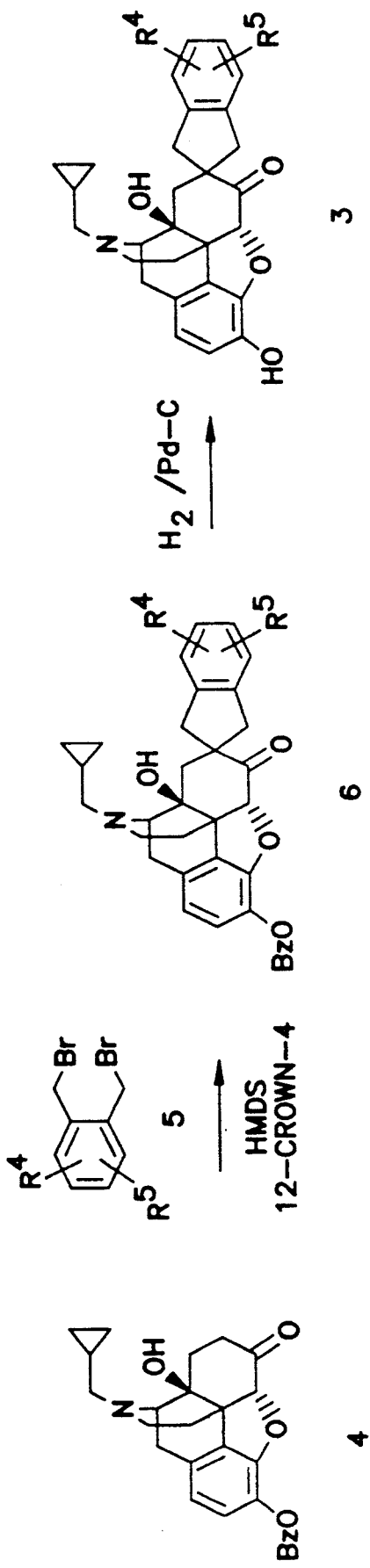

When $OR^3$ and/or $R^2$ are base-liable groups such as acyl or alkanoxy, the protecting groups can be replaced by art-recognized methodologies for the protection/deprotection of hydroxyl groups. Of course, the free hydroxyl groups in the compounds of formula I or II can be also converted to alkanoyloxy groups by methods known to the art, i.e., by reaction with an anhydride or acyl halide in the presence of base.

The structures, common names and Merck Index reference numbers of representative 4,5-epoxy-6-ketomorphinan starting materials of general formula (III) are summarized on Table I, below.

TABLE I

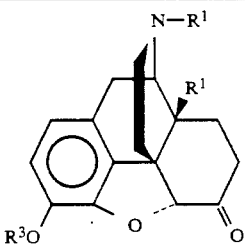

| $R^1$ | $R^2$ | $R^3$ | Common Name | Merck No.[2] |
|---|---|---|---|---|
| $CH_2CH(CH_2)_2$ | OH | H | naltrexone | 6209 |
| $CH_3$ | OH | H | oxymorphone | 6837 |
| $CH_3$ | H | H | hydromorphone | 4714 |
| $CH_3$ | H | $CH_3$ | hydrocodone | 4687 |
| $CH_2CH(CH_2)_2$ | H | H | — | — |
| $CH_2CH=CH_2$ | OH | H | naloxone | 6208 |
| $CH_3$ | OH | $CH_3$ | oxycodone | 6827 |

[1]Preparation, M. Gates et al., J. Med. Chem., 7, 127 (1964).
[2]The Merck Index, W. Windholz, ed., Merck & Co., Rahway, NJ (10th ed. 1983).

Other starting materials of formula III can be prepared by synthetic methods which are well known in the art of organic chemistry. For example, compounds of formula III wherein $R^1$ is H and $R^3$ is a suitable protecting group, and wherein the 6-keto group has also been protected, can be prepared from compounds on Table I. These intermediates can be N-alkylated and deprotected to yield compounds of formula III wherein $R^1$ is $C_2$-$C_5$(alkyl), $C_4$-$C_6$(cycloalkyl)alkyl, $C_5$-$C_7$(cycloalkenyl)alkyl, aryl, aralkyl, trans-$C_4$-$C_5$-alkenyl or furan-2-ylakyl, by the application of well-known reactions. The 6-keto group may also be replaced by methylene using methods known tot he art. This would yield compounds of formula I or II which are 6-deoxy analogues.

Also, the free hydroxyl groups of compounds of formula III, e.g., $R^2$=OH and/or $R^3$=H, can be protected by acid-labile groups such as tetrahydropyranyl, trimethylsilyl, 1-methoxy-isopropyl and the like as disclosed in Compendium of Organic Synthetic Methods, I. T. Harrison et al., eds., Wiley-Interscience, New York, N.Y. (1971) at pages 124–131, (hereinafter "Compendium"). The protection of the 6-keto group of compounds of Table I by its reversible conversion into a ketal or a thioketal group is disclosed in Compendium, at pages 449–453. Methods for the demethylation of N-methyl amines have been disclosed, for example, in Compendium at page 247, J. Amer. Chem. Soc., 89, 1942 (1967) and J. Amer. Chem. Soc., 77, 4079 (1955).

Procedures for the alkylation of secondary amines with halides under basic or neutral conditions are well known. For example, see Compendium at pages 242–245; Org. Synth., 43, 45 (1963); J. Org. Chem., 27, 3639 (1962) and J. Amer. Chem. Soc., 82, 6163 (1960).

Compounds of formula III wherein $R^2$ is acyloxy and/or $R^3$ is acyl can be prepared by using the corresponding starting materials on Table I. For example, naltrexone can be diacylated by reacting it with the appropriate ($C_1$-$C_5$)alkyl anhydride for 10–18 hrs at 18°–25° C. The resultant 3,14-diacylated compound can be converted to the 14-acylated compound by limited hydrolysis. The 3-acylated starting materials can be prepared by the short-term reaction of the compounds of Table I with the anhydride, e.g., for about 2–4 hours. The 3-acylated product can be separated from the 3,14-diacylated product by chromatography.

The acid salts of compounds of formula I or II, wherein $R^3$=H, can be converted into the corresponding ($C_1$-$C_5$)alkoxy derivatives [$R^3$=($C_1$-$C_5$)alkyl] by dissolving the starting material in DMF and adding an excess of the appropriate ($C_1$-$C_5$)alkyl iodide and an amine such as diisopropylethylamine. The reaction can be conducted at an elevated temperature for about 4–10 hours. The final product can be purified by column chromatography.

The invention also comprises the pharmaceutically acceptable salts of the biologically active compounds of formula I or II, together with a pharmaceutically acceptable carrier for administration in effective, non-toxic dose form. Pharmaceutically acceptable amine salts may be salts of organic acids, such as acetic, citric, lactic, malic, tartaric, p-toluene sulfonic acid, methane sulfonic acid, and the like as well as salts of pharmaceutically acceptable mineral acids such as phosphoric, hydrochloric or sulfuric acid, and the like.

These physiologically acceptable salts are prepared by methods known in the art, e.g., by dissolving the free amine bases with an excess of the acid in aqueous alcohol.

The formulae and physical data of representative compounds of formula I and II is summarized on Table II, below.

In the clinical practice of the present method, the compounds of the present invention will normally be administered orally or parenterally, as by injection or infusion, in the form of a pharmaceutical unit dosage form comprising the active ingredient in combination with a pharmaceutically acceptable carrier, which may be a solid, semi-solid or liquid diluent or an ingestible capsule or tablet. The compound or its salt may also be used without carrier material. As examples of pharmaceutical carriers may be mentioned tablets, intravenous solutions, suspensions, controlled-release devices, microcapsules, liposomes and the like. Usually, the active

TABLE II

Physical Data for Spiroindanonaltrxone Derivatives and related compound.

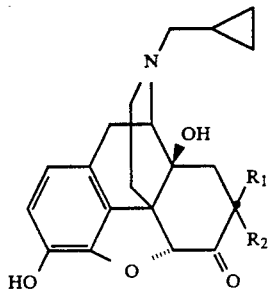

| Compd No | $R_1 R_2$ | Formula (FW) | mp °C. | yield (%)[1] | yield (%)[2] |
|---|---|---|---|---|---|
| 3a | (indane) | $C_{28}H_{29}NO_4 \cdot HCl(480.009)$ | >280 | 72 | 75 |
| 3b[3] | (indane-OMe) | $C_{29}H_{31}NO_5 \cdot HCl(510.035)$ | >280 | 46 | 73 |
| 3c[3] | (indane-OMe) | $C_{29}H_{31}NO_5 \cdot HCl \cdot 2H_2O(546.059)$ | 225–230(decomp) | 83 | 63 |
| 3d | (naphthyl-fused) | $C_{32}H_{31}NO_4 \cdot HCl \cdot H_2O(548.077)$ | 248–253(decomp) | 68 | 68 |
| 3e[3] | (naphthyl-fused) | $C_{32}H_{31}NO_4 \cdot HCl \cdot 1.5H_2O$ | 240–250(decomp) | 42 | 64 |
| 13 | (acenaphthyl) | $C_{32}H_{31}NO_4 \cdot HCl(530.069)$ | >280 | 79 | 74 |

[1] Yield of coupling reaction.
[2] Yield of deprotection.
[3] Mixture of resioisomers.

substance will comprise between about 0.05 and 99%, or between 0.1 and 95% by weight of the resulting pharmaceutical unit dosage form, for example, between about 0.5 and 20% of preparation intended for injection or infusion and between 0.1 and 50% of preparation, such as tablets or capsules, intended for oral administration.

Since naltrexone has been evaluated clinically to assess its ability to inhibit ethanol consumption by alcoholic patients undergoing outpatient treatment, and NTI has been evaluated for its ability to block opiate tolerance and dependence in animal models, effective dosages of the compounds of the present invention can be extrapolated from doses found to be effective in such studies, as well as from the dosages of NTI found to be effective to decrease ethanol consumption in the rat model.

The present compounds are believed to be able to suppress ethanol ingestion or opiate self-administration for prolonged periods of time, following administration of a single dose, e.g., by administration of a single unit dosage form. As used herein, the term "suppression" is intended to mean that the alcohol- or drug-addicted human will either abstain entirely from ethanol or opiate ingestion for a period of time following administration of a dose of the present compounds, or will ingest substantially less, e.g., at least about 15-50% less, of his or her baseline ethanol or opiate intake, i.e., before recovery. Preferably, administration of the present compounds can suppress ethanol or opiate intake for at least about 12-24 hours, most preferably for at least about 48 hours. The term "opiate" as used herein is intended to encompass all of the morphinan-based analgesics, including but not limited to, morphine, heroin, codeine, hydrocodone, and the pharmaceutically acceptable salts thereof. See, *Remington's Pharmaceutical Sciences*, A. Osol, ed., Mack Pub. Co. (16th ed. 1980) at pages 1043–1084.

The invention will be further described by reference to the following detailed examples, wherein melting points were determined in open capillary tubes with a Thomas-Hoover melting point apparatus and are uncorrected. Analysis were performed by M-H-W Laboratories, Phoenix, Ariz. NMR spectra were recorded at ambient temperature on a GE 300 MHz spectrometer. Mass spectra were obtained on a Finnigan 40000, a AEIMS-30, or a VG7070EHF spectrometer. All reagents and solvents were reagent grade. Naltrexone was supplied by Mallinckrodt.

EXAMPLE 1

Bisbromomethylbenzene Derivatives

Method I.(a) 2,3-Bisbromomethylanisole. A mixture of 2,3-dimethylanisole (5.0 g, 36.5 mmol), N-bromosuccinimide (13.0 g, 73.4 mmol) and benzoylperoxide (40 mg) in carbontetrachloride (75 mL) was refluxed for 15 hrs. The resulting succinimide was removed by filtration and the filtrate was concentrated in vacuo. The residue was chromatographed on silica gel (chloroform-hexane, 1:4) and then recrystallized from ether-hexane to afford 2,3-bisbromomethylanisole (8a, $R^4=1$-OMe, $R^5=H$) (5.4 g, 68%), mp 78°–79° C.; $^1$H NMR (CDCl$_3$) δ 3.82(3H, s), 4.63(2H, s), 6.84(1H, dd, J=8.4, 2.4 Hz), 6.91(1H, d, J=2.4 Hz), 7.30(1H, d, J=8.4 Hz).

(b) 3,4-Bisbromomethylanisole (8b, $R^4=1$-OMe, $R^5=H$) was prepared by Method I to yield 65%, mp 49°–50° C.; $^1$H NMR (CDCl$_3$) δ 3.90(3H, s), 4.62(2H, s), 4.75(2H, s), 6.87(1H, d, J=8.4 Hz), 6.98(1H, d, J=8.4 Hz), 7.27(1H, t, J=8.4 Hz).

(c) (2,3-Bisbromomethyl)nitrobenzene (8c, $R^4=1$-NO$_2$, $R^5=H$) was prepared by Method I to yield 51%, mp 64°–65° C.; $^1$H NMR (CDCl$_3$) δ 4.68(2H, s), 4.85(2H, s), 7.47(1H, t, J=7.8 Hz), 7.64(1H, dd, J=7.8 Hz, 1.5 Hz), 7.88(1H, dd, J=7.8 Hz, 1.5 Hz).

(d) (3,4-Bisbromomethyl)nitrobenzene (8d, $R^4=1$-NO$_2$, $R^5=H$) was prepared by Method I to yield 53%, oil; $^1$H NMR (CDCl$_3$) δ 4.66(2H, s), 4.67(2H, s), 7.56(1H, d, J=8.4 Hz), 8.15(1H, dd, J=8.4 Hz, 2.4 Hz), 8.25(1H, d, J=2.4 Hz).

(e) (2,3-Bisbromomethyl)fluorobenzene (8e, $R^4=1$-F, $R^5=H$) was prepared by Method I to yield 77%, oil; $^1$H NMR (CDCl$_3$) δ 4.50(2H, s), 4.70(2H, d, J=1.5 Hz), 7.05(1H, t, J=8.0 Hz), 7.15(1H, d, J=8.0 Hz), 7.26(1H, dd, J=8.0 Hz, 4.0 Hz).

(f) 1,2-Bisbromomethylnaphthalene (8f, $R^4=R^5=3,4$-benzo) was prepared by Method I to yield 82%, mp 149°–150° C.; $^1$H NMR (CDCl$_3$) δ 4.77(2H, s), 5.10(2H, s), 7.43(1H, d, J=8.7 Hz), 7.54(1H, m), 7.64(1H, m), 7.85(2h, m), 8.15(1H, d, J=8.7 Hz).

Method 11(a). 2,3-Bishydroxymethylnaphthalene (11, $R^4=R^5=5,6$-benzo). To a suspension of LAH in THF (50 mL) was added a solution of dimethyl 2,3-naphthalenedicarboxylate (5.4 g, 22.1 mmol) in THF (20 mL) and the mixture was refluxed for 18 hrs. The cooled mixture was poured into ice water, neutralized with HCl and extracted with EtOAc. The extract was washed with water, dried over anhydrous MgSO$_4$ and concentrated. The resulting crystals of 2,3-bishydroxymethylnaphthalene (2.8 g, 67%) were collected on a glass filter and dried in vacuo. Mp 160°–161° C.; $^1$H NMR (CDCl$_3$) δ 4.67(4H, d, J=4.8 Hz), 5.23(2H, t, J=4.8 Hz), 7.42(2H, m), 7.85(4H, m). The filtrate was concentrated and hexane was added. The resulting crystals of 2-hydroxymethyl-3-methylnaphthalene (0.7 g, 21%) were collected. Mp 125°–126° C.; $^1$H NMR (CDCl$_3$) δ 4.67 (4H, d, J=4.8 Hz), 5.23 (2H, t, J=4.8 Hz), 7.42 (2H, m), 7.85 (4H, m).

(b). 1,8-Bishydroxymethylnaphthalene (15) was prepared by Method II to yield 53%, mp 157°–158° C.; $^1$H NMR (DMSO-d$_6$) δ 5.05(4H, d, J=6.0 Hz), 5.25(2H, d, J=6.0 Hz), 7.42(2H, d, J=8.0 Hz), 7.59(2H, d, J=8.0 Hz), 7.83(2H, d, J=8.0 Hz).

Example 2

(a). 2,3-Bisbromomethylnaphthalene (8 g) ($R^4=R^5=5,6$-benzo).

To a solution of 2,3-bishydroxymethylnaphthalene was added PBr$_3$ and the mixture was refluxed for 1 hr and then cooled. The mixture was diluted with water and the product was extracted with EtOAc. The extract was washed with aqueous sodium bicarbonate, dried and the solvent removed. The residue was recrystallized from chloroform-hexane to afford 2,3-bisbromomethylnaphthalene (2.7 g, 81%). Mp 147°–148° C.; $^1$H NMR (CDCl$_3$) δ 4.89(4H, s), 4.52(2H, m), 7.81(2H, m), 7.87(2H, s).

(b). 1,8-Bisbromomethylnaphthalene (16) was prepared from 15 in accord with Example 2(a) to yield 83%, mp 131°–132° C.; $^1$H NMR (CDCl$_3$) δ 5.31(4H, s), 7.46(2H, t, J=14.7 Hz), 7.63-(2H, d, J=14.7 Hz), 7.89(2H, d, J=14.7 Hz).

Example 3

3-Benzylnaltrexone (4)

To a solution of naltrexone (2.5 g, 7.3 mmol) and benzylbromide (1.5 g, 8.8 mmol) in DMF (25 mL) was added potassium carbonate (2.8 g, 20 mmol). The mixture was stirred for 12 hrs at 60° C., then cooled and diluted with water. The resulting oily product was extracted with EtOAc. The extract was washed with water dried over MgSO$_4$ and concentrated. The residue was chromatographed on silica gel (hexane-EtOAc, 3;2) to afford 3-benzylnaltrexone (4) (2.3 g, 74%). $^1$H NMR (CDCl$_3$) δ 0.15(2H, m, H-20β, H-21β), 0.56(2H, m, H-20α, H-21α), 0.87(1H, m, H-19), 1.58(1H, dd, J=12.3 Hz, 2.4 Hz, H-15), 1.64(1H, dt, J=13.5 Hz, 2.4 Hz, H-8), 1.89(1H, d, J=13.5 Hz, H-8), 2.13(1H, dt, J=12.3 Hz, 2.4 Hz, H-15), 2.30(1H, dt, J=12.3 Hz, 2.4 Hz, H-16), 2.40(3H, m, H-7, H-18), 2.55(1H, dd, J=18.3 Hz, 6.0 Hz, H-10), 2.69(1H, dd, J=12.3 Hz, 2.4Hz, H-16), 3.03(2H, m, H-7, H-10), 3.18(1H, d, J=6.0 Hz, H-9), 4.70(1H, s, H-5), 5.20(1H, d, J=12.0 Hz, Bz CH), 5.29(1H, d, J=12.0 Hz, Bz CH), 6.56(1H, d, J=7.2 Hz, H-1), 6.71(1H, d, J=7.2 Hz, H-2), 7.25-7.60(5H, m, Bz aromatic H).

Example 4

3-Benzyl-7-(4'-methoxy-2'-spiroindano)naltrexone and 3-benzyl-7-(7'-methoxy-2'-spiroindano)naltrexone (6b)

To a solution of hexamethyldisilazane (0.4 mL, 1.8-mmol) and 12-crown-4 (0.24 g, 1.38 mmol) in THF (4 mL) was added a 2.5M solution of n-BuLi in hexane (0.54 mL, 1.38-mmol) at −78° C. with stirring. After stirring for 10 min, a solution of 3-benzylnaltrexone (200 mg, 0.46 mmol) in THF, (2 mL) was added followed by a solution of 2,3-bisbromomethylanisole (8a) (320 mg, 1.5 mmol). The mixture was allowed to stand for 15 min at 25° C. and then refluxed for 3 hrs. The mixture was diluted with brine and the product was extracted with EtOAc. The extract was washed with brine, dried and the solvent removed. The residue was chromatographed on silica gel (hexane-EtOAc, 4:1) to afford a mixture of 3-benzyl-7-(4'-methoxy-2'-spiroindano)naltrexone and 3-benzyl-7-(7'-methoxy-2'-spiroindano)-naltrexone (217 mg, 83%); high-resolution MS (FAB), (M+H) 564.2772 5 (calcd. for C$_{36}$H$_{38}$NO$_5$ 564.2750). $^1$H NMR (CDCl$_3$) δ 0.14(2H, m, H-20β, H-21β), 0.55(2H, m, H-20α, H-21α), 0.85(1H, m, H-19), 1.56(1H, d, J=12.3 Hz, H-15), 1.70(1H, broad s, 14-OH), 1.83(1H, d, J=13.5 Hz, H-8), 2.06(1H, d, J=13.5 Hz, H-8), 2.10(1H, m, H-15), 2.37(1H, d, J=17.1 Hz, indane CH), 2.35-2.55(3H, m, H-16, H-18), 2.58(1H, hidden, 1H, H-10), 2.71(1H, d, J=8.4 Hz), 3.03(1H, d, J=18.3 Hz, H-10), 3.13(1H, d, J=4.8 Hz, H-9), 3.21 and 3.23(1H, d, J=17.1 Hz, indane CH), 3.52 and 3.54(1H, d, J=17.1 Hz, indane CH), 3.75(1H, d, J=17.1 Hz, indane CH), 3.78 and 3.80(3H, s, OMe), 5.01 and 5.06(1H, s, H-5), 5.21(1H, d, J=12.3 Hz, Bz CH$_2$), 5.36(1H, d, Bz aromatic H), 6.74(1H, d, J=7.5 Hz, H-2), 6.78(1H, d, J=7.5 Hz, Bz aromatic H). The ratio of the two regioisomers was 20:19.

Example 5

3-Benzyl-7-(5'-methoxy-2'-spiroindano)naltrexone and 3-benzyl-7-(6'-methoxy-2,-spiroindano)naltrexone (6c) were prepared by the procedure of Example 4 using 8b:

$^1$H NMR (CDCl$_3$) δ 0.15(2H, m, H-20β, H-21β), 0.55(2H, m, H-20α, H-21α), 0.86(1H, m, H-19), 1.25(1H, broad s, OH), 1.57(1H, d, J=9.9 Hz, H-15), 1.82 and 1.83(1H, d, =13.2 Hz, H-8), 2.04(1H, d, J=13.2 Hz, H-8), 2.11(1H, t, J=10.8 Hz, H-15), 2.33(1H, d, J=14.4 Hz, indane CH), 2.40(2H, m, H-18), 2.48(1H, m, H-16), 2.58(1H, dd, J=18.3, 3.6 Hz, H-10), 2.71(1H, d, J=11.1 Hz), 3.03(1H, d, J=18.3 Hz, H-10), 3.13-(1H, d, J=4.8 Hz, H-9), 3.18 and 3.20(1H, d, J=16.8 Hz, indane CH), 3.43 and 3.46(1H, d, J=16.8 Hz, indane CH), 3.79(1H, d, J=16.8 Hz, indane CH), 4.07(3H, s, OMe), 5.02-(1H, s, H-5), 5.21(1H, d, J=12.3 Hz, Bz CH$_2$), 5.36(1H, d, J=12.3 Hz, Bz CH$_2$), 6.58(1H, d, J=8.4 Hz, H-1), 6.63-6.75(2H, m, indane aromatic H), 6.74(1H, d, J=8.4 Hz, H-2), 6.74(1H, d, J=8.4 Hz, indane aromatic H), 7.04(1H, m, indane aromatic H), 7.25-7.50(5H, m, Bz aromatic H). The ratio of the two isomers was 10:7.

Example 6

3-Benzyl-7-(5',6'-benz-2'-spiroindano)naltrexone (6d)

was prepared by the procedure of Example 4 using 8e: $^1$H NMR (CDCl$_3$) δ 0.1 5(2H, m, H-20β, H-21β), 0.55(2H, m, H-20α, H-21α), 0.86(1H, m, H-19), 1.59(1H, d, J=12.3 Hz, 2.4 Hz, H-15), 1.87(1H, broad s, 14-OH), 1.87(1H, d, J=14.7 Hz, H-8), 2.05(1H, d, J=14.7 Hz, H-8), 2.05(1H, d, 2.13(1H, t, J=9.6 Hz, H-15), 2.39(2H, m, H-16), 2.54(1H, d, J=15.9 Hz, indane CH), 2.54(2H, hidden, 1H, H-18), 2.66(1H, m, H-10), 3.04(1H, d, J=18.3 Hz, H-10), 3.14(1H, d, J=3.6 Hz, H-9), 3.40(1H, d, J=16.3 Hz, indane CH), 3.64(1H, d, J=16.3 Hz, indane CH), 3.95(1H, d, J=15.9 Hz, indane CH), 5.03(1H, s, H-5), 5.21(1H, d, J=11.1 Hz, Bz CH$_2$), 5.35(1H, d, J=11.1 Hz, Bz CH$_2$), 6.59(1H, d, J=8.7 Hz, H-1), 6.75(1H, d, J=8.7 Hz, H-2), 7.25-7.50(7H, m, naphthalene H, Bz aromatic H), 7.60(2H, s, naphthalene H), 7.72(2H, m, naphthalene H).

Example 7

3-Benzyl-7-(4',5'-benz-2'-spiroindano)naltrexone and 3-benzyl-7-(6',7'-benz-2'-spiroindano)naltrexone (6e)

was prepared by the procedure of Example 4, using 8f: $^1$H NMR (CDCl$_3$) δ 0.14(2H, m, H-20β, H-21β), 0.50(2H, m, H-20α, H-21α), 0.87(1H, m, H-19), 1.43(1H, d, J=14.4 Hz, H-15), 1.90 and 1.93(1H, d, 14.2 Hz, H-8), 2.12(1H, broad s, 14-OH), 2.15(1H, J=14.2 Hz, H-8), 2.25-2.80(6H, m, H-10, H-15, H-16, H-18, indane CH), 2.54(2H, hidden, 1H, H-18), 3.05(1H, d, J=18.6 Hz, H-10), 3.15(1H, d, J=4.8 Hz, H-9), 3.36 and 3.56(1H, d, J=17.0 Hz, indane CH), 3.74 and 3.99(1H, d, J=15.8 Hz, indane CH), 4.18(1H, d, J=16.2 Hz, indane CH), 5.07 and 5.08(1H, s, H-5), 5.22(1H, d, J=12.0 Hz, Bz CH$_2$), 5.35(1H, d, J=12 OHz, Bz CH$_2$), 6.59(1H, d, J=8.2 Hz, H-1), 6.75 and 6.76(1H, d, J=8.2 Hz, H-2), 7.20-7.60(8H, m, naphthalene H, Bz aromatic H), 7.60-7.90(3H, s, naphthalene H). The ratio of the two regioisomers was 11:7.

Example 8

3-Benzyl-7-(2',3'-dihydro = 2'-spiroperinaphtheno)-naltrexone (12)

was prepared by the procedure of Example 4 using 16: $^1$H NMR (CDCl$_3$) δ 0.06(2H, m, H-20β, H-21β), 0.48(2H, m, H-20α, H-21α), 0.76(1H, m, H-19), 1.48-(1H, d, J=13.2 Hz, H-8), 1.60(1H, dd, J=12.3, 2.4 Hz, H-15), 1.79(1H, d, J=13.2 Hz, H-8), 2.05(1H, m, H-15), 2.29(2H, m, H-18) 2.45(1H, hidden, H-16), 2.50(1H, broad s, 14-OH), 2.52(1H, d, J=18.3 Hz, H-10), 2.57(1H, d, J=15.9 Hz, 4H-naph), 2.72(1H, dd, J=12.3, 5.1 Hz, H-16), 2.91(1H, s, H-9), 2.94-(1H, d, J=18.3 Hz, H-10), 3.42(1H, d, J=15.9 Hz, 4H-naph CH), 3.45(1H, d, J=15.9 Hz, 4H-naph CH), 3.92(1H, d, J=15.9 Hz, 4H-naph CH), 5.04(1H, s, H-5), 5.24(1H, d, J=12.0 Hz, Bz CH), 5.34(1H, d, J=12.0 Hz, Bz CH), 6.55(1H, d, J=8.4 Hz, H-1), 6.76(1H, d, J=8.4 Hz, H-2), 7.13(1H, d, J=3.6 Hz, naphthalene H), 7.20–7.60(8H, m, Bz aromatic H and naphthalene H), 7.66(1H, d, J=8.4 Hz, naphthalene H), 7.70(1H, d, J=8.7 Hz, naphthalene H).

Example 9

7-(4,-Methoxy-2,-spiroindano)naltrexone and 7-(7'-Methoxy-2'-spiroindano)-naltrexone (3b).

A solution of a mixture of 3-benzyl-7-(4'-methoxy-2'-spiroindano)naltrexone and 3-benzyl-7-(7'-methoxy-2'-spiroindano)naltrexone (170 mg, 0.3 mmol) in EtOH was hydrogenated with a few drops of c-HCl on 10% Pd-C for 10 hrs. The catalyst was removed by filtration and the filtrate was concentrated. To the residue, EtOAc and aqueous sodium bicarbonate solution was added and shaken well. The organic layer was separated, dried and concentrated. The residue was chromatographed on silica gel (hexane-EtOAc, 2:1) to afford 7-(4'-methoxy-2'-spiroindano)naltrexone (90 mg, 63%). This compound was dissolved in EtOH and a few drops of c-HCl was added. A solution was concentrated and the residue was dissolved in EtOH again and diethyl ether was added. The resulting white solid was collected, washed with ether and dried to afford the hydrogenchloride salt of a mixture of 7-(4'-methoxy-2'-spiroindano)naltrexone and 7-(7'-methoxy-2'-spiroindano)naltrexone (3b) (75 mg, purification yield, 75%, mp 225°–230° C. (decomp.)); high-resolution MS (FAB), (M+H$^+$) 474.2281 C(calcd. for C$_{29}$H$_{32}$NO$_5$ 474.2280), $^1$H NMR (CDCl$_3$) δ 0.13(2H, m, H-20β, H-21β), 0.54(2H, m, H-20α, H-21α), 0.85(1H, m, H-19), 1.52(1H, d, J=12.0 Hz, H-15), 1.82(1H, d, J=9.0Hz, H-8), 2.04(1H, d, J=9.0 Hz, H-8), 2.04(1H, d, J=9.0 Hz, H-8), 2.12(1H, t, J=12.0 Hz, H-15), 2.29(1H, d, J=15.9 Hz, indane CH), 2.32–2.50(3H, m, H-16, H-18), 2.57(1H, dd, J=18.3 Hz, 4.8 Hz, H-10), 2.70(1H, d, J=8.7 Hz, H-16), 3.03(1H, d, J=18.3 Hz, indane CH), 3.14(1H, d, J=2.7 Hz, H-9), 3.18 and 3.21(1H, d, J=15.6 Hz, indane CH), 3,47 and 3.50(1H, d, J=15.6 Hz, indane CH), 3.74(1H, d, J=18.3 Hz, indane CH), 3.77 or 3.80(3H, s, OMe), 4.96 and 4.99(1H, s, H-5), 6.60(1H, d, J=8.7 Hz, H-1), 6.63(1H, d, J=8.4 Hz, indane aromatic H), 6.73(1H, d, J=8.7 Hz, H-2), 6.75(1H, hidden, indane aromatic H), 7.10(1H, t, J=8.4 Hz, indane aromatic CH).

The following compounds were prepared from the corresponding 3-benzo compounds using the procedure of Example 9.

Example 10

7-(5'-Methoxy-2'-spiroindano)naltrexone and 7-(6'-Methoxy-2'-spiroindano)naltrexone (3c)

$^1$H NMR (CDCl$_3$) δ 0.14(2H, m, H-20β, H-21β), 0.54(2H, m, H-20α, H-21α), 0.85(1H, m, H-19), 1.25(1H, s, OH), 1.53(1H, dd, J=13.2 Hz, 2.4 Hz, H-15), 1.81 and 1.82(1H, d, J=13.4 Hz, H-8), 2.03(1H, d, J=14.4 Hz, H-8), 2.13(H, dt, J=12.3 Hz, 2.4 Hz, H-15), 2.32(1H, d, J=15.9 Hz, indane CH), 2.39(2H, m, H-18) 2.46(1H, dd, J=12.3 Hz, 3.6 Hz, H-16), 2.56(1H, dd, J=19.5 Hz, 6.0 Hz H-10), 2.70(1H, dd, J=12.3 Hz, 3.6 Hz, H-16), 3.03(1H, d, 3.40 or 3.42(1H, d, J=15.9 Hz, indane CH), 3.76(3H, s, OMe), 3.78(1H, d, J=14.7 Hz, indane CH), 4.95 and 4.96(1h, s, H-5), 6.59(1H, d, J=8.7 Hz, H-1), 6.64–6.72(2H, m, indane aromatic H), 6.73(1H, d, J=8.7 Hz, H-2), 7.03(1H, t, J=7.2 Hz, indane aromatic CH). Exact mass (FAB) calcd for C$_{29}$H$_{32}$NO$_5$ (M+H)$^+$ 474 2280, found 474.2281.

Example 11

7-(5',6'-Benz-2'-spiroindano)naltrexone (3d)

$^1$H NMR (CDCl$_3$) δ 0.14(2H, m, H-20β, H-21β), 0.54(2H, m, H-20α, H-21α), 0.85(1H, m, H-19), 1.25(1H, s, 14-OH), 1.51-(1H, dd, J=12.3 Hz, 2.4 Hz, H-15), 1.86(1H, d, J=14.7 Hz, H-8), 2.04(1H, d, J=14.7 Hz, H-8), 2.12(H, dt, J=12.3 Hz, 3.6 Hz, H-15), 2.39(2H, m, H-18, H-16), 2.53(1H, d, J=16.8 Hz, indane CH), 2.56(1H, dd, J=18.3 Hz, 6.0 Hz H-10), 2.69(1H, d, J=18.3 Hz, H-16), 3.03(1H, d, J=18.3 Hz, H-10), 3.13(1H, d, J=4.8 Hz, H-9), 3.37(1H, d, J=16.8 Hz, indane CH), 3.58(1H, d, 6.60(1H, d, J=8.7 Hz, H-1), 6.73(1H, d, J=8.7 Hz, H-2), 7.37(2H, m, naphthalene H), 7,59(2H, s, naphthalene H), 7.73(2H, m, naphthalene H). Exact mass (FAB) calcd for C$_{32}$H$_{32}$NO$_4$ (M+H)$^+$ 494.2331, found 494.2334.

Example 12

7-(4',5'-Benz-2'-spiroindano)naltrexone and 7-(6',7'-Benz-2'-spiroindano)naltrexone (3e)

$^1$H NMR (CDCl$_3$) δ 0.16(2H, m, H-20β, H-21β), 0.56(2H, m, H-20a, H-21α), 0.87(1H, m, H-19), 1.56(1H, dd, J=14.4 Hz, 2.4 Hz, H-15), 1.83 and 1.95 (1H, d, J=14.2 Hz, H-8), 2.15(2H, m, H-8, 14-OH), 2.30–2.80 (6H, m, H-10, H-15, H-16, H-18, indane H), 3.05 (1H, d, J=18.6 Hz, H-10), 3.18(1H, d, J=4.8 Hz, H-9), 3.30 and 3.52 (1H, d, J=16.8 Hz, indane CH), 3.68 and 3.95 (1H, d, J=15.8 Hz, indane CH), 4.18 (1H, d, J=17.0 Hz), 4.98 and 5.02 (1H, s, H-5), 6.60(1H, d, J=8.2 Hz, H-1), 6.74(1H, d, J=8.2 Hz, H-2), 7.20–7.60 (4H, m, naphthalene H), 7,65(1H, m, naphthalene H), 7.90(H, m, naphthalene H). Exact mass (FAB) calcd for C$_{32}$H$_{32}$NO$_4$ (M+H)$^+$ 494.2331, found 494.2334.

Example 13

7-(2',3'-Dihydro-2'-spiroperinaphtheno)naltrexone (13)

$^1$H NMR (CDCl$_3$) δ 0.06(2H, m, H-20β, H-21β), 0.48(2H, m, H-20α, H-21α), 0.76(1H, m, H-19), 1.48(1H, d, J=14.4 Hz, H-8), 1.57(1H, d, J=12.9 Hz, H-15), 1.79(1H, d, J=14.4 Hz, H-8), 2.09(1H, dt, J=2.4 Hz, 12.0 Hz, H-15), 2.30–(2H, m, H-18), 2.44(1H, hidden, H-16), 2.50(1H, broad s, OH), 2.51(1H, dd, J=18.3 Hz, 2.4 Hz H-10), 2.57(1H, dd, J=15.9 Hz, 4H-naphthalene CH), 2.70(1H, dd, J=12.3 Hz, 3.9 Hz, H-16), 2.91(1H, s, H-9), 2.94(1H, d, J=18.3 Hz, H-10), 3.39(1H, d, J=14.4 Hz, 4H-naphthalene CH), 3.43(1H, d, J=14.4 Hz, 4H=naphthalene CH), 3.93(1H, d, J=15.9 Hz, naphthalene CH), 4.99(1H, d, J=2.4 Hz, H-5), 6.10(1H, broad s, phenol OH) 6.57(1H, dd, J=8.4 and 2,4 Hz, H-1), 6.73(1H, dd, J=8.4 Hz, 2.4 Hz, H-1), 7.10–7.75(6H, m, naphthalene). Exact mass (FAB) calcd for C$_{32}$H$_{32}$NO$_4$ (M+H)$^+$ 494.2331, found 494.2350.

Example 14

3-O-Benzyl-17-(cyclopropylmethyl)-4,5α-epoxy-14-hydroxymorphinan-6-one-7-(spiro-2'-indane)

To a solution of 0.63 mL, 2.9 mmol of hexamethyldisilazane in 5 mL of dry DMSO was added 1.6 mL, 2.56 mmol of a 1.6M solution of n-butyl lithium in hexanes under nitrogen. The reaction was stirred for 15 min at 25° C., then a solution of 0.70 g, 1.29 mmol of 3-benzylnaltrexone in 4 mL of DMSO was added and stirred for 15 min. Then a solution of 1.2 g, 4.6 mmol of α,α'-dibromo-o-xylene in 2 mL of DMSO was added. The reaction was kept at 25° C. for 1 hr and then poured into 50 mL of H$_2$O. To the mixture was added 10 mL of brine and the mixture was then extracted with 4×30 mL of ethylacetate. The combined extracts were washed with 10 mL of brine, dried (anhyd. Na$_2$SO$_4$), and the solvent was evaporated under vacuum. The residue was chromatographed using radial thin layer chromatography (2 mm plate, elution with 5% MeOH/CHCl$_3$). The solvent was evaporated under vacuum to give 250 mg, 36.3% of a solid. This material was further purified by vacuum-flash chromatography (1"×5" column, elution with hexane-ethylacetate [8:1]) to give 160 mg, 23.2% yield of a white foam.

For analytical purposes, 120 mg of the indane was chromatographed on a 0.5 mm preparatory thin layer chromatography plate (elution with hexane/ethylacetate [3:1]). The free base was liberated from the silica gel with CHCl$_3$. The solvent was evaporated under vacuum and the residue was dissolved in 10 mL of ether. The ether solution was filtered and ethereal HCl was added to precipitate the HCl salt as a white solid, 86.2 mg, 60.4% purification yield; mp 271°-272° C. dec: IR (KBr, cm$^{-1}$) 1721.2 (6—C=O); m/e 533 (M$^+$); CHN.

Example 15

17-(Cyclopropylmethyl)-4,5α-epoxy-14-hydroxymorphinan-6-one-7-(spiro-2'-indane) (3a)

A solution of 0.16 g, 0.3 mmol of the benzyl ether (8) in 50 mL of absolute EtOH and 1.5 ml of concentrated HCl was hydrogenated at 25° C. and 50 psig for 48 hr over 35 mg of 10% Pd/C (Fluka). The catalyst was then removed by filtering through Celite in a fritted glass funnel. The filtrate was washed with 3×25 mL portions of EtOH. The filtrate and washings were combined and the solvent was removed under vacuum. The residue was dissolved in 20 mL of CHCl$_3$ and 1 mL of EtOH and stirred with 20 mL of sat. NaHCO$_3$ for 10 min. The basic mixture was extracted with 3 ×35 mL portions of CHCl$_3$, washed with 10 mL of brine and the solvent was evaporated under vacuum to give 100 mg, 75.2% of crude product. This material was further purified by spinning thin layer chromatography (2 mm chromatotron plate, elution with hexane/ethyl acetate [3:1]). Fractions containing the product were pooled and the solvent was removed under vacuum. The residue was dissolved in ethanol/ether and ethereal HCl was added to precipitate the HCl salt. This material was recrystallized from MeOH/ether to give a white solid 34.9 mg, 24.2%.

For analytical purposes, 100 mg of the product was chromatographed on the chromatotron (2 mm plate, elution with hexane/ethylacetate [3:1]) to provide 54 mg of white solid after evaporation of the solvent. The solid was dissolved in EtOH/ether and the HCl salt was precipitated with ethereal HCl. The salt was collected and recrystallized once from MeOH/ether to give 34.9 mg, 35.0% purification yield of 3a as a white solid; mp: >285° C.: IR (KBr, cm$^{-1}$) 1718.1 (6—C=O); $^1$H NMR (CDCl$_3$) δ 0.133 (m, 2 H, H-19β, H-20β, 0.525 (m, 2 H, H-19α, H-20α), 0.842 (m, 1 H, H-18), 1.52 (dd, 1 H, H-15e), 1.80 (d, 1 H, H-8), 2.05 (d, 1 H, H-8), 2.57 (dd, 1 H, H-10e), 2.69 (dd, 1 H, H-16e), 3.02 (d, 1 H, H-10a), 3.11 (d, 1 H, H-9), 3.18 (d, 1 H, indane-CH$_2$), 3.48 (d, 1 H, indane-CH$_2$), 3.82 (d, 1 H, indane-CH$_2$), 4.9.5 (s, 1 H, H-5), 6.57 (d, 1 H, H-1), 6.71 (d, 1 H, H-2), 7.11 (m, 4 H, indane-CH), 5.66 (bs, 1 H, phenol-OH), 1.89 (bs, 1 H, 14-OH); m/e 444 (M$^+$); CHN. Calcd for C$_{28}$H$_{30}$NO$_4$Cl.1/5 H$_2$O: C, 69.54; H, 6.34; N, 2.9 Found: C, 69.87, H, 6.53; N, 2.76.

Example 16

Evaluation of Antagonist and Agonist Activity

A. Smooth Muscle Assays

1. Guinea Pig Ileal Longitudinal Muscle (GPI). Ilea from guinea pigs were taken approximately 10 cm from the ileocecal junction, and a strip of longitudinal muscle with the myenteric plexus attached was prepared by the method of H. B. Rang et al., *Brit. J. Pharmacol.*, 22, 356 (1964). A 1 cm portion of this strip was then mounted between two platinum electrodes placed in a 10 ml organ bath and connected to an isometric transducer; contractions were recorded on a polygraph. Contractions of the ileal strip were initiated by supramaximal rectangular pulses in all preparations (80 V of 0.5 ms duration at a frequency of 0.1 Hz). Krebs bicarbonate solution containing 1.25 μM chlorpheniramine maleate was the bathing solution and was continuously bubbled with 95% O$_2$ and 5% CO$_2$. The organ bath was maintained at 36°-37° C. The longitudinal muscle strip was allowed to equilibrate with continuous stimulation for a minimum of 90 min. Cumulative concentration-response curves were determined after drugs were added to the bath in 10- to 50-μl amounts and washed out with two 10 ml portions of buffer after noting their maximum effects.

2. Mouse Vas (MVD). This assay was performed according to the description by G. Henderson et al., *Brit. J. Pharmacol.*, 46, 764 (1972). Both vasa deferentia were dissected out of mice and mounted singly through two platinum ring electrodes in a 10 ml organ bath. The bath contained Krebs bicarbonate solution that was continuously bubbled with 95% O$_2$ and 5% CO$_2$. The organ bath was maintained at 37° C. The tissue was attached to an isometric transducer and stimulated transmurally with rectangular pulses (0.1 Mz, 1 ms duration, supramaximal voltage). Drugs were added cumulatively to the bath in 10- to 50-μl amounts and washed out after noting their maximum effect.

B. Pharmacology

Each compound (100 nM) was incubated for 15 min with the mouse vas deferens (MVD) and guinea pig ileum (GPI) preparations prior to adding graded doses of a standard agonist for determination of an IC$_{50}$ value. The standard agonists employed were [D-Ala$^2$, D-Leu$^5$-]enkephalin (DADLE), morphine, and ethylketazocine (EK); these are selective for delta (DADLE), mu (M) and kappa (EK) opioid receptors. Concentration-response curves were obtained in the absence (control) and the presence of the antagonist are expressed as IC$_{50}$ values. The IC$_{50}$ ratio represents the IC$_{50}$ in the presence of the antagonist divided by the control IC$_{50}$ value in the same tissue. Therefore, a high IC$_{50}$ ratio represents a correspondingly high degree of antagonism at a particular receptor. This IC$_{50}$ ratio was employed to calculate the Ke value using the equation Ke=[antagonist]/(IC$_{50}$ ratio-1). Therefore, a low Ke represents a correspondingly high degree of binding at a particular receptor. The results of these bioassays are summarized on Table III, below.

TABLE III

Activity of Spiroindanonaltrexones and its related compound.

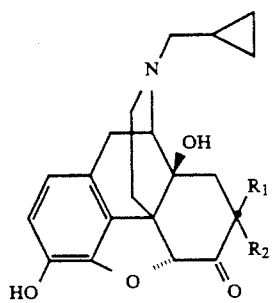

| Compound R₁, R₂ | | GPI Agonism IC$_{50}$ (nM) | Potency | Antagonism Ratio[1] (Morphine) | Ratio[2] (EK) | MVD Agonism IC$_{50}$ (nM) | Antagonism Ratio[3] (DADLE) |
|---|---|---|---|---|---|---|---|
| Morphine | | 316 | 1 | — | — | — | — |
| (indane) | 3a | | | ($K_e$ = 41.0) | — | — | ($K_e$ = 0.78) |
| (OMe indane) | 3b | (−15.0%) | — | 8.47 ($K_e$ = 13.4 nM) | 2.63 | (23.1%) | 60 ($K_e$ = 1.71 nM) |
| (OMe indane) | 3c | (−8.8%) | — | 0.92 | 2.41 | (10.5%) | 14 ($K_e$ = 7.81 nM) |
| (naphthyl) | 3d | 253 | 0.47 | 0.97 | 0.18 | (15.4%)[4] | 428 ($K_e$ = 0.234 nM) |
| (naphthyl) | 3e | (20.3%)[4] | — | 0.53 | 2.01 | (15.6%) | 25 ($K_e$ = 4.17 nM) |
| (phenalene) | 3f | (16.0%) | — | 0.89 | 0.39 | (13.0%) | 8 ($K_e$ = 14.9 nM) |

[1]Morphine IC$_{50}$/Morphine + Compound IC$_{50}$.
[2]EK IC$_{50}$/EK + Compound IC$_{50}$.
[3]DADLE IC$_{50}$/DADLE + Compound IC$_{50}$.
[4]% Inhibition at 1000 nM Of these compounds, 3d is the most potent antagonist ($K_e$ = 0.234 nM) of δ-selective agonist. Compound 3a also has a potent δ-antagonist activity ($K_e$ = 0.78 nM). Compound 3b has a moderate δ-antagonist activity ($K_e$ = 1.71 nM). Other compounds have weaker δ-antagonist activities. All compounds have no agonist activity for δ-receptors and no antagonist activity for κ-receptors. Surprisingly, compound 3d has a potent agonist activity (the relative potency of this compound to morphine is 0.47) for μ-receptors along with δ-antagonist activity.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of the formula:

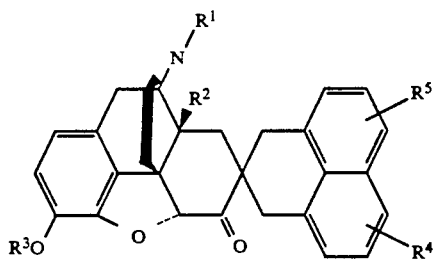

wherein $R^1$ is $(C_1-C_5)$alkyl, $C_3-C_6$(cycloalkyl)alkyl, $C_5-C_7$(cycloalkenyl)alkyl, $(C_6-C_{12})$aryl, $(C_6-C_{12})$aralkyl, trans$(C_4-C_5)$alkenyl, allyl or furan-2-ylalkyl, $R^2$ is H, OH or $O_2C(C_1-C_5)$alkyl; $R^3$ is H, $(C_6-C_{12})$aralkyl, $(C_1-C_5)$alkyl; or $(C_1-C_5)$alkylCO; and $R^4$ and $R^5$ are individually H, F, Cl, Br, $NO_2$, $NH_2$, $(C_1-C_5)$alkyl, $(C_1-C_5)$alkoxy or together are dioxymethylene (—OCH$_2$O—) or benzo; and the pharmaceutically acceptable salts thereof.

2. The compound of claim 1 wherein $R^3$ is H.
3. The compound of claims 1 or 2 wherein $R^2$ is OH.
4. The compound of claim 1 wherein $R^1$ is $C_3-C_6$(cycloalkyl)alkyl.
5. The compound of claim 1 wherein $R^4$ is $(C_1-C_5)$alkoxy and $R^5$ is H.
6. The compound of claim 5 wherein $R^4$ is methoxy and $R^5$ is H.
7. The compound of claim 1 wherein $R^4$ and $R^5$ together are benzo.
8. The compound of claim 1 wherein $R^3$ is H, $R^2$ is OH and $R^1$ is cyclopropylmethyl.

9. The compound of claim 8 wherein $R^4$ is 4'-methoxy or 7'-methoxy and $R^5$ is H.
10. The compound of claim 8 wherein $R^4$ and $R^5$ together are 4,5-benzo or 5,6-benzo.
11. The compound of claim 8 wherein $R^4$ is $NO_2$ and $R^5$ is H.
12. A compound of the formula:

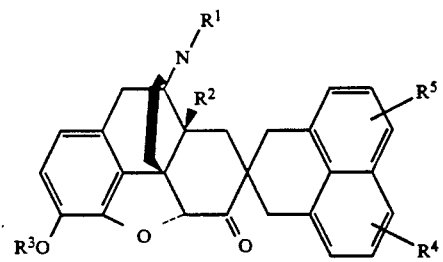

wherein $R^1$ is $(C_1-C_5)$alkyl, $C_3-C_6$(cycloalkyl)alkyl, $C_5-C_7$-(cycloalkenyl)alkyl, $(C_6-C_{12})$aryl, $(C_6-C_{12})$aralkyl, trans$(C_4-C_5)$alkenyl, allyl or furan-2-ylalkyl, $R^2$ is H, OH or $O_2C(C_1-C_5)$alkyl; $R^3$ is H, $(C_6-C_{12})$aralkyl, $(C_1-C_5)$alkyl; or $(C_1-C_5)$alkylCO; and $R^4$ and $R^5$ are individually H, F, Cl, Br, $NO_2$, $NH_2$, $(C_1-C_5)$alkyl, $(C_1-C_5)$alkoxy or together are dioxymethylene (—OCH$_2$O—) or benzo, wherein $R^4$ and $R^5$ can occupy any available site on the naphthyl ring; and the pharmaceutically acceptable salts thereof.

13. The compound of claim 12 wherein $R^3$ is H.
14. The compound of claim 12 wherein $R^2$ is OH.
15. The compound of claims 13 or 14 wherein $R^1$ is $C_3-C_6$-(cycloalkyl)alkyl.
16. The compound of claim 15 wherein $R^1$ is cyclopropylmethyl.
17. The compound of claim 12 wherein $R^4$ is H and $R^5$ is H.

* * * * *

UNITED STATES PATENT AND TRADEMARK OFFICE
CERTIFICATE OF CORRECTION

PATENT NO. : 5,298,622
DATED : Mar. 29, 1994
INVENTOR(S) : Portoghese et al.

It is certified that error appears in the above-indentified patent and that said Letters Patent is hereby corrected as shown below:

Column 19, lines 5-15
In claim 1, please delete

" 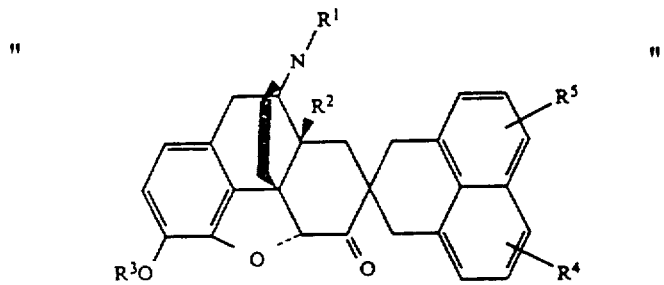 "

and insert therefor

-- 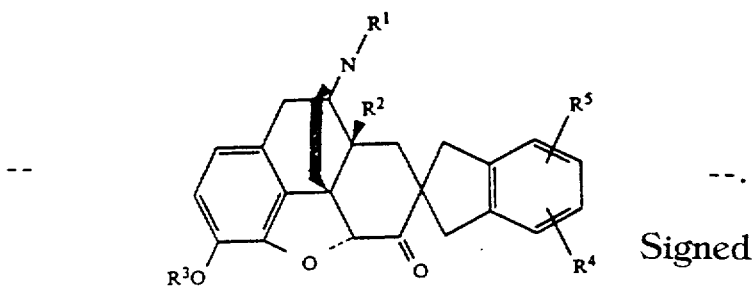 --.

Signed and Sealed this

Sixteenth Day of January, 1996

Attest:

BRUCE LEHMAN

Attesting Officer

Commissioner of Patents and Trademarks